United States Patent [19]

Beattie et al.

[11] Patent Number: 5,175,209
[45] Date of Patent: Dec. 29, 1992

[54] POROUS WAFER FOR SEGMENTED SYNTHESIS OF BIOPOLYMERS

[75] Inventors: Kenneth L. Beattie; James D. Frost, III, both of The Woodlands, Tex.

[73] Assignee: Baylor College of Medicine, Houston, Tex.

[21] Appl. No.: 648,808

[22] Filed: Jan. 31, 1991

Related U.S. Application Data

[63] Continuation-in-part of Ser. No. 462,999, Jan. 8, 1990, abandoned, which is a continuation of Ser. No. 716, Jan. 6, 1987, abandoned.

[51] Int. Cl.$^5$ .................... C08G 63/48; C08G 63/91; C08F 283/00
[52] U.S. Cl. .................... 525/54.11; 530/333; 530/334; 422/131; 422/134
[58] Field of Search .................... 525/54.1, 54.11; 422/69, 70, 131, 134; 530/333, 334

[56] References Cited

U.S. PATENT DOCUMENTS

| | | | |
|---|---|---|---|
| 3,692,669 | 9/1972 | Bauman | 210/198.2 |
| 3,763,879 | 10/1973 | Jaworek | 210/232 |
| 4,155,846 | 5/1979 | Novak et al. | 210/198.2 |

OTHER PUBLICATIONS

Matteucci et al, "Synthesis of Deoxyoligonucleotides on a Polymer Support" J. Am. Chem. Soc., vol. 103, pp. 3185-3191 (1981).

Bannwarth et al, "A System for Simultaneous Chemical Synthesis of Different DNA Fragments on Solid Support" DNA, vol. 5, No. 5, 1986 pp. 413-419.

*Primary Examiner*—Nathan M. Nutter
*Attorney, Agent, or Firm*—Fulbright & Jaworski

[57] ABSTRACT

A wafer for synthesizing biopolymers which includes a solid phase support material, a reaction chamber which receives and retains the support material and at least one inert porous material which allows flow through the wafer. Also included is a segmented wafer synthesis device comprising at least one, and preferably numerous, wafers for the simultaneous synthesis of multiple defined-sequenced biopolymers. Further there are process steps for synthesizing a variety of biopolymers. Synthetic polynucleotides have played a key role in studies of genetic organization through their use as primers for DNA sequencing and as hybridization probes, linkers and adapters in the cloning of genes.

32 Claims, 7 Drawing Sheets

POROUS WAFER FOR SEGMENTED SYNTHESIS OF BIOPOLYMERS

The present invention was made utilizing government funds and thus the government has been granted a royalty free non-exclusive license.

This application is a continuation-in-part of copending U.S. patent application Ser. No. 07/462,999 filed Jan. 8, 1990 and now abandoned which was a continuation of copending U.S. patent application Ser. No. 07/000,716 filed Jan. 6, 1987 (now abandoned).

BACKGROUND OF THE INVENTION

The present invention relates to the chemical synthesis of biopolymers, and specifically, to a device for the simultaneous synthesis of large numbers of biopolymers, for example, polynucleotides, polypeptides and polysaccharides. The development of methods for the chemical synthesis of biopolymers of any desired sequence has resulted in great advances in many areas of biology and medicine during recent years. For example, physical and biochemical studies of the structure and interactions of synthetic DNA fragments has led to important new findings concerning the molecular mechanisms of genetic processes, including DNA metabolism, and regulation of gene expression. Synthetic polynucleotides have played a key role in studies of genetic organization through their use as primers for DNA sequencing and as hybridization probes, linkers and adapters in the cloning of genes, of genes. An additional use of synthetic polynucleotides is in DNA probe technology in the diagnosis of disease. Ultimately, synthetic polynucleotides may be used in gene replacement therapy to cure genetic disorders, and in other genome engineering procedures to provide resistance to disease and starvation. Synthetic polynucleotides are routinely used for site-directed in vitro mutagenesis, for studying the structure-function relationships within genetic regulatory elements and for determining the effects of specific amino acid substitutions on the functions of proteins. The latter use, termed protein engineering, will not only facilitate an understanding of the mechanism of action of enzymes and other proteins, but will also permit the design of functionally superior proteins and drugs, leading to important advancements in medicine, agriculture and industry. Likewise, the availability of synthetic defined-sequence polypeptides is bringing about equally dramatic advancements in protein chemistry, immunology, pharmacology and biotechnology.

In many genetic engineering projects it is necessary to use a large number of differently defined sequence polynucleotides, sometimes hundreds of different sequences in a single experiment. Similarly, some protein chemistry experiments require hundreds of different peptide sequences. In order to determine the nucleotide sequence of the human genome millions of different polynucleotide primers will be required. The latter endeavor, along with many other worthwhile projects that could be carried out by individual laboratories, are economically impractical with the current cost to the investigator of synthetic polynucleotides ($5-$10 per nucleotide residue).

The capability to chemically synthesize polynucleotides of defined sequence resulted from the pioneering work of Michelson and Todd in the 1950s, (Michelson, A.M. & Todd, Sir 20 A. R., "Nucleotides Part XXXII. Synthesis of a Dithymidine Dinucleotide Containing a 3':5' Internucleotide Linkage," *J. Chem. Soc.*-1955, pp. 2632 2638), in which a method was developed for specific chemical synthesis of 5'-3' internucleotide phosphodiester linkages. This procedure was developed further over the next 20 years, culminating in the total synthesis of a gene for transfer RNA by Khorana and Associates, (Khorana, H.G., "Total Synthesis of a Gene," *Science*, Vol. 203, pp. 614–625, (1979). Recently, the phosphate diester method has been replaced by the phosphate triester method (Letsinger, R.L. and Ogilvie, K.K., "A Convenient Method for Stepwise Synthesis of Oligothymidylate Derivatives in Large-Scale Quantities," *J. Am. Chem. Soc.*, Vol. 89, pp. 4801–4803, (1967); Narong, S.A., Brousseau, R., Hsiung, H.M. and Michniewicz, J.J. "Chemical Synthesis of Deoxyoligonucleotides by the Modified Triester Method, *Meth. Enzymol*, Vol. 65, pp. 610–620, (1980)) and the phosphite triester method (Letsinger, R.L., Finnan, J.L., Heavener, G.A. and Lunsford, W.B., "Phosphite Coupling Procedure for Generating Internucleotide Links," *J. Am. Chem. Soc.*, Vol. 97, pp. 3278–3279, (1975); Beaucage, S.L. and Caruthers, M.H., "Deoxynucleotide Phosphoramidites—A New Class of Key Intermediates For Deoxypolynucleotide Synthesis," *Tet. Lett.*, Vol. 22, pp. 1859–1862, (1981)), which have the advantage of more rapid synthesis and fewer side reactions. Both of these methods can be carried out in solution as originally devised, and have been adapted for solid phase synthesis of polynucleotides (Matteucci, M.D. and Caruthers, M.H., "Synthesis of Deoxyoligonucleotides on a Polymer Support," *J. Am. Chem. Soc.*, Vol. 103, pp. 3185–3191, (1981); Sproat, B.S. and Bannwarth, W., "Improved Synthesis of Oligodeozynucleotides On Controlled Pore Glass Using Phosphotriester Chemistry and a Flow System," *Tet. Lett.*, Vol. 24, pp. 5771–5774, (1983)). Solid phase synthesis offers the advantage of greater speed of synthesis because the growing chain is covalently attached to an insoluble support, permitting reagents to be washed away between chemical steps and obviating the need to purify the polynucleotide product after each addition of monomer. Furthermore, solid phase synthesis permits automation of the process, so that each base addition (via multistep reaction cycle) can be carried out in about ten minutes at ambient temperature. The high efficiency of condensation under these conditions (currently 99%) permits the automated synthesis of polydeoxynucleotides of chain length greater than 100.

Chemical procedures used for solid phase synthesis of polypeptides are frequently based on the original protocol of Merrifield, which was successfully used for synthesis of enzymically active, 124-residue ribonuclease A (Gutte, B. and Merrifield, R.B., "The Synthesis of Ribonuclease A," *J. Biol. Chem.*, Vol. 246, pp. 1922–1941, (1971)). This procedure uses standard polystyrene-divinylbenzene supports, t-butyloxycarbonyl (Boc) amino group protection, and DCC-activated condensation with symmetric anhydride intermediates. The procedure has been used successfully in automated peptide synthesizers, as well as in the multiple simultaneous synthesis method of Houghton described below.

Several alternate procedures for peptide synthesis have been devised. One particularly advantageous one (Auffret, A.D. and Meade, L.G., "Alternative Strategies in Peptide Synthesis," *Synthetic Peptides in Biology and Medicine*, Alitalo, K., Partanen, P. and Vaheri, A. (Eds.), Elsevier Science Publishers, Amsterdam, 1985) utilizes a composite polyamide-Kieselguhr support (found to be superior for continuous flow synthesis), fluorenylemethozycarbonyl (Fmoc) amino group protection, and 1-hydrozybenzatriazole-activated condensation with pentafluorophenyl ester (PFPE) intermediates. The high stability of the active ester intermediates make them more conveniently used for peptide synthesis than the relatively unstable anhyride intermediates.

Recent developments in polynucleotide synthesis, including descriptions of the chemical reactions, are summarized in review articles by John Smith ("Automated Solid Phase Oligodeoxyribonucleotide Synthesis", *American Biotechnology Laboratory*, pp. 15-24 (December 1983)) and Marvin Caruthers ("Gene Synthesis Machines: DNA Chemistry and Its Uses", *Science*, Vol. 230, pp. 281-85 (1985)). One particularly promising recent advancement is the development of cost effective procedures for in situ generation of phosphoramidite intermediates from inexpensive protected nucleosides (Barone, A.D., Tang, J.Y. and Caruthers, M.H., "In Situ Activation of Bis-Dialkylaminophosphines—A New Method for Synthesizing Deoxyoligonucleotides on Polymer Supports," *Nucl. Acids Res.*, Vol. 12, pp. 4051-4061, (1984); Nielsen, J., Taagaard, M., Marigg, J.E., van Boom, J.H. and Dahl, 0., "Application of 2-cyanoethyl N, N, N', N'-tetraisopropylphosphorodiamidite for In Situ Preparation of Deolyribonucleoside Phosphoramidites and Their Use in Polymer—Supported Synthesis of Oligodeoxyribonucleotides," *Nucl. Acids Res.*, Vol. 14, pp. 7391-7403, (1986)).

Another advantageous recent development is the use of amidine groups to protect exocyclic amino groups (e.g., Caruthers, M.H., McBride, L.J., Bracco, L.P. and Dubendorff, J.W., "Studies on Nucleotide Chemistry 15. Synthesis of Oligodeoxynucleotides Using Amidine Protected Nucleosides," *Nucleosides and Nucleotides*, Vol. 4, pp. 95-105, (1985)). Amidine protecting groups stabilize deolyadenosine residues against acid-catalyzed depurination, which occurs during the detritylation step of the synthesis cycle, thereby permitting synthesis of longer polynucleotides.

Finally, a procedure for synthesis of RNA polymers on silica supports, involving a modified phosphoramidite approach, has recently been reported (Kierzek, R., Caruthers, M.H., Longfellow, C.E., Swinton, D., Turner, D.H. and Freier, S.M., "Polymer-Supported RNA Synthesis and its Application to Test the 5 Nearest—Neighbor Model for Duplez Stability," *Biochemistry*, Vol. 25, pp. 7840-7846, (1986)).

Although the above methods permit the synthesis of one or a few polynucleotide sequences at a time, at moderate cost, there is a great need for technological development in this area, to reduce the cost of synthesis and to permit simultaneous synthesis of large numbers of polynucleotide sequences. Progress toward this aim has recently been made in the form of procedures and devices that permit multiple simultaneous synthesis of polynucleotides or polypeptides.

Frank et al. ("A New General Approach for the Simultaneous Chemical Synthesis of Large Numbers of Oligonucleotides: Segmented Solid Supports", *Nucleic Acid Research*, Vol. 11, No. 13, pp. 4365-77 (1983)) recently used cellulose filters as a solid phase support for polynucleotide synthesis. A protected nucleoside was covalently linked to the hydroxyl groups of the filter paper by 3'-o-succinate linkage, then elongated by the phosphate triester procedure used previously with loose beaded solid phase support materials. Frank et al. reported synthesis of two octamers, and proposed that by stacking the paper filters into four different reaction columns, designated for addition of A, G, C and T residues to the growing chain and sorting the discs between reaction cycles, a large number of different polynucleotide sequences could be simultaneously synthesized. Frank, et al. demonstrated that the two octamers synthesized by this procedure (present within the same reaction column during most cycles) were obtained at reasonable yield, and DNA sequence analysis proved that the products consisted of the expected nucleoside sequences and were not contaminated by each other.

The proposed use of the filter paper method for simultaneous synthesis of many sequences was later implemented by Matthes et al. ("Simultaneous Rapid Chemical Synthesis of Over One Hundred Polynucleotides on a Microscale", *The EMBO Journal*, Vol. 3, No. 4, pp. 801-05 (1984)). These authors used a phosphate triester procedure similar to that reported by Frank et al., to simultaneously synthesize over one hundred polynucleotide sequences within a period of two weeks. Several limitations of the Matthes et al. procedure exist. Due to low loading capacity of the filter paper disks, their hydrophilic nature and their unfavorable mass transfer properties, the coupling efficiency at each step is poor compared with that attained with the standard solid phase synthesis procedures, and only a very small quantity of desired polynucleotide is produced, of limited chain length (up to about 20-mer). The product is heavily contaminated by shorter failure sequences, and must be purified by time-consuming procedures before use. Nevertheless, this procedure has the potential of yielding large numbers of sequences at low cost. This method apparently has been attempted by many laboratories, but apparently only a very few laboratories have been able to obtain usable products using the technique.

Another report (Bannwarth, W. and Laiza, P., "A System for the Simultaneous Chemical Synthesis of Different DNA Fragments on Solid Support," *DNA*, Vol. 5, pp. 413-419, (1986)) describes a mechanical apparatus that can simultaneously synthesize several different polynucleotides. The device consists of a series of stackable rotatable metal disks, each containing, in radially symmetrical position, a single reaction chamber plus a number of narrow "bypass" holes. The stacked metal disks can be rotated to produce vertical alignment of all reaction chambers designated for addition of a given nucleoside residue to the support-bound DNA chains contained therein, with these chambers being connected by bypass holes. Thus, by appropriate rotation of the metal disks following each reaction cycle (created by sequential flow of reagents and solvents through the system), a different DNA sequence is synthesized for each of the stacked metal disks. The chief advantage of this device over the segmented filter paper method is higher coupling efficiency, enabled by the placement of controlled pore glass supports within the reaction chambers. DNA chains of up to 36 residues long were produced utilizing phosphoramidite chemistry. Another advantage of the design is its potential for automation. The chief disadvantage is the relatively low number of simultaneous synthesis (a maximum of 12 DNA fragments were simultaneously produced).

In another approach, utilized for simultaneous synthesis of different polypeptides, (Houghten, "General Method for the Rapid Solid-Phase Synthesis of Large Numbers of Peptides: Specificity of Antigen-Antibody Interaction of the Level of Individual Amino Acids", *Proc. Natl. Acad. Sci. USA*, Vol. 82, pp. 5131-35 (August 1985)), Houghten employed polypropylene mesh bags containing solid phase support resins used for standard solid phase synthesis of peptides. By placing a number of these resin-containing bags into a single stirred reaction chamber, all peptide sequences to which a given amino acid was to be added could undergo the coupling reaction simultaneously. The authors used this procedure to simultaneously synthesize 248 different 13-mer peptides which were obtained in yield comparable to that attained by standard single-peptide solid phase methods. In this work, each of the 13-mer peptides actually consisted of a sequence identical to the "control sequence," except for a single amino acid replacement. Thus, at each amino acid addition, the vast majority of the resin-containing bags were placed into the same stirred reaction vessel, while only those resins containing peptides to which a unique amino acid was to be added at that position in the sequence were reacted separately from the bulk of the material. Although the "different" peptide sequences synthesized in Houghten's original work each consisted of the same sequence, with a single amino acid change from the "control sequence," it was proposed that by use of a multiplicity of stirred reaction vessels, each containing many resin-containing bags, the procedure could be used for simultaneous synthesis of a large number of completely unique peptide sequences. Houghten's "tea bag" method, including description of its use for simultaneous synthesis of 120 entirely different 15-residue peptides, is further described in Houghten et al, "Simultaneous Multiple Peptide Synthesis: The Rapid Preparation of Large Numbers of Discrete Peptides for Biological Immunological, and Methodological Studies," *Biotechniques*, Vol. 4, No. 6, pp. 525-28 (1986).

Two difficulties may prevent the Houghten "tea bag" method from being implemented for simultaneous synthesis of large numbers of polynucleotide sequences. The sealable polypropylene mesh bags are not sufficiently inert to be used in the phosphate triester and phosphite triester procedures currently used for polynucleotide synthesis. Support containing porous bags constructed of inert materials such as TEFLON are difficult, if not impossible to seal, making it difficult to prevent loss of solid phase support from the bags during synthesis. A more serious problem is that in the solid phase procedure for polynucleotide synthesis, sufficient space must be left in the column above the support bed, such that as solvents and reagents are pumped from below, the support is "lifted" by the upward flow, resulting in the necessary mass transfer within the beads required for nearly quantitative chemical reactions. The physical properties of the non-rigid "tea bags" would not permit the necessary lifting of support materials during passage of solvents and reagents through the column.

Accordingly, due to the shortcomings of the present devices and procedures, there exists a need for a device and procedure for rapid, simultaneous synthesis of large numbers of any biopolymer of different sequences at high yields and lower costs.

SUMMARY OF THE INVENTION

It is therefore an object of the present invention to provide an improved device for the chemical synthesis of biopolymers.

Another object of the present invention is to provide an improved device for the simultaneous synthesis of large numbers of biopolymers.

Yet another object of the present invention is to provide for the simultaneous production of large numbers of defined-sequence biopolymers at very low cost.

Another object of the present invention is to provide a device applicable for the simultaneous, solid phase synthesis of any of the various biopolymers.

Still yet another object of the present invention is to provide for the simultaneous production of large numbers of defined-sequence biopolymers at high yields.

Yet an additional object of the present invention is to provide an improved segmented device for simultaneously producing biopolymers.

A further object of the present invention is to provide an improved device for simultaneously producing large numbers of biopolymers requiring lower amounts of reagents and solvents.

Yet a further object of the present invention is to provide an improved device for simultaneously producing large numbers of biopolymers requiring less synthesis time.

A still further object of the present invention is to provide an improved device for simultaneously producing large numbers of biopolymers in which the many segments, hereinafter referred to as "wafers", are easy to separate from one another after each reaction cycle.

An additional object of the present invention is to provide an improved solid phase support segment ("wafer") for the chemical synthesis of biopolymers.

Thus, in accomplishing the foregoing objects, there is provided in accordance with one aspect of the present invention, a segmented wafer synthesis device for the synthesis of multiple defined-sequence biopolymers, comprising a solvent delivery system, at least one column connected to the solvent delivery system to provide solvent and reagent flow through the column, and at least one wafer positioned in the column at which polymeric synthesis occurs. In a preferred embodiment, the synthesis device comprises at least four columns for receiving four reagents, and a plurality of wafers in each column, wherein each of the wafers provides for the synthesis of a defined-sequence polymer. The device can be either automatic, semi-automatic or manual, depending on user needs.

In a further embodiment, the device comprises a plurality of stacked wafers which are connected together to form a column with the solvent delivery system being connected to the column to provide flow through the column.

In accordance with another aspect of the present invention, there is provided a wafer for synthesizing biopolymers, for example, polynucleotides, polypeptides and polysaccharides, comprising a solid phase support material, a retaining ring for retaining the support material in a chamber formed by the inner walls of the retaining ring, and means, for example, a membrane or frit, for allowing flow through the retaining ring to the support material and for preventing migration of the support material from the retaining ring. Preferably, the retaining ring comprises an inner, enclosed reaction chamber for receiving and retaining the support material, the retaining ring being open on both ends. The porous flow means is an essentially inert porous material, and is preferably provided at each end of the retaining ring and extends across the inner chamber to enclose the chamber. In addition, the wafer preferably comprises an inert securing means for securing the support materials to the retaining means.

The solid phase support material advantageously is selected from the group consisting of silica, controlled pore glass (CPG), polystyrene-divinyl-benzene, polyamide resins, polyamide-Kieselguhr composite resins, macroreticular resins, benzhydrylamine resins, and macroporous plastic resins such as MONOBEADS resin (a resin produced by Pharmacia). The porous support material comprises a derivatized material which includes a covalently attached residue, for example, a nucleoside in the case of polynucleotide synthesis.

The porous membrane or frit preferably comprises flexible membrane composed of TEFLON or other inert fluorocarbons, or rigid frits of glass, stainless steel or titanium. The porosity of the membrane or frit is sufficiently large to allow flow through the wafer and sufficiently small to retain the porous support material in the wafer.

In one preferred embodiment, the wafer comprises a solid phase support material, an inner housing ring comprising an inner reaction chamber formed by the inner walls of the ring for receiving and retaining the support material, the housing ring being open on both ends, an inert porous membrane or frit positioned at and extending across each of the open ends of the housing ring, the membrane having a larger diameter than the inner ring, and two outer rings having an inner diameter slightly larger than the inner ring, the inner rings encompassing the inner ring and securing the edges of the membrane between the inner ring and the outer rings. Particularly preferred is an outer securing means which comprises a retaining ring positioned about the outer surface of each end of the housing ring.

In another preferred embodiment, the wafer comprises a solid phase support material, an inert cylindrical housing ring, open on both ends, and an inert circular frit snapped into indentations near the open ends of the housing ring.

The wafer design of the present invention provides for the simultaneous production of numerous biopolymers. The geometry of the support material results in high coupling efficiency, and the rigid wafers are easy to sort after each reaction cycle. This arrangement permits the simultaneous synthesis of many different sequences. By using support material of varying capacity (density of derivatization) and by varying the height of each wafer, the scale of synthesis can be varied from less than 0.1 micromole to greater than 10 micromoles per segment. Furthermore, segments of varying heights can be stacked within each column, permitting the simultaneous synthesis of products of widely different scale. The flexibility and efficiency of this approach should permit the synthesis of large numbers of biopolymers at a substantially reduced cost. For example, the present cost of polynucleotide synthesis, under ideal conditions (such as existence of an in-house synthesis service) is typically $5 to $10 per residue. With the segmented wafer device, the cost is significantly less, and possibly as low as $0.50-$2.00 per residue. Since cost presently remains the limiting factor in the use of synthetic biopolymers, development of the segmented wafer device is another quantum leap in the use of biopolymers in scientific research, and should accelerate future developments in biomedical science.

Further objects, features and advantages will become apparent from a review of the detailed description of the preferred embodiments which follows, in view of the drawings, a brief description of which follows.

BRIEF DESCRIPTION OF THE DRAWINGS

Referring to the drawings.

All numerical references in the figures will be consistent such that the same part in different figures will have the same number.

DETAILED DESCRIPTION OF PREFERRED EMBODIMENTS

The present invention will first be described by reference to the drawings. At various points in the following disclosure, the present invention is discussed in terms of polynucleotide synthesis. The invention, as has been noted, is equally applicable and useful for the production of any biopolymer that can be synthesized on solid phase supports. Furthermore, the following discussion and drawings primarily describe and illustrate one specific wafer design. It is understood that this description is for illustrative purposes only, and other wafer designs are possible and within the scope of the present invention.

In the present invention, a chemically inert wafer is defined as a wafer where all the surfaces except the biopolymer elongation point of the wafer which are in contact with the reagents or derivative maintain integrity in the presence of iodine and pH above 9.0 and below 3.0.

As used herein, biopolymers include polynucleotides, polypeptides, polysaccharides, glycopeptides, lipopolysaccharides, lipopeptides and functional or structural analogs.

Figure 1:
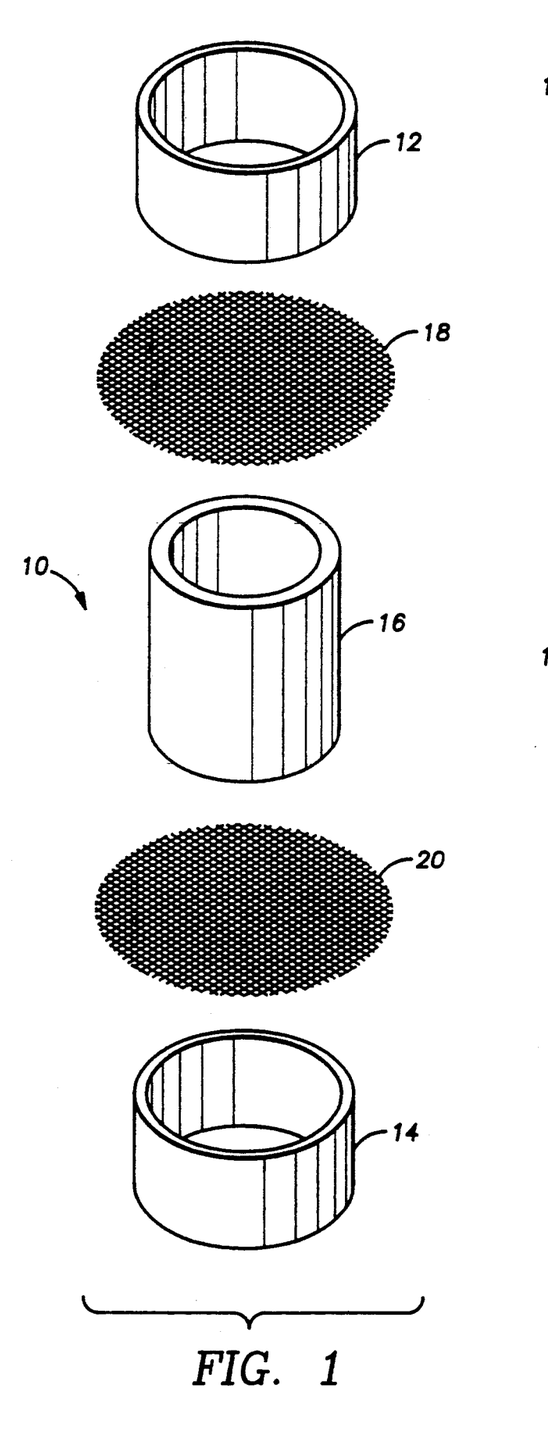
FIG. 1 is an exploded perspective view of an embodiment of the wafer of the present invention.

FIG. 1 illustrates the wafer 10 of the present invention prior to assembly, i.e., in an exploded schematic view. The wafer comprises an outer securing means comprising upper and lower retaining rings 12 and 14. Located between the opposing retaining rings 12 and 14 is an internal housing ring 16, which together with membranes 18 and 20 serves as the reaction chamber. The wafer further includes porous materials 15 or membranes 18 and 20 or porous materials 15 positioned at and extending across either end of the housing ring 16 and secured between the housing ring 16 and the retaining rings 12 and 14.

The housing ring 16 has an outer diameter just slightly smaller than the inner diameter of the retaining rings 20, 12 and 14. The porous membranes 18 and 20 have outer diameters greater than the outer diameters of the retaining rings. It is to be noted that ring, as used here in referring to both the inner housing ring and the retaining rings, includes both circular, rectangular, square and other geometric variations in 25 ring design. The important design criteria is that the rings have a hollow interior space for retaining the reactant components, as described below.

Figure 2:
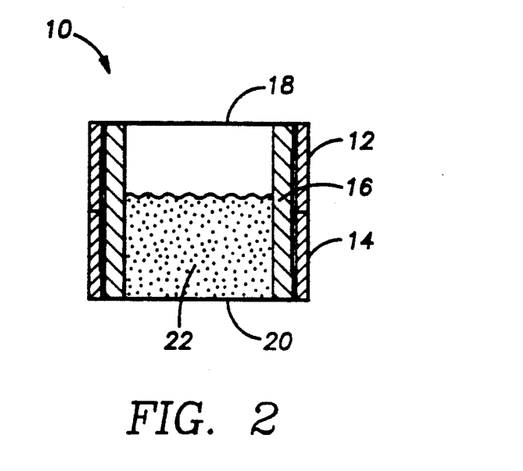
FIG. 2 is a cross-sectional view of an embodiment of the wafer of the present invention in its assembled state.
Figure 3:
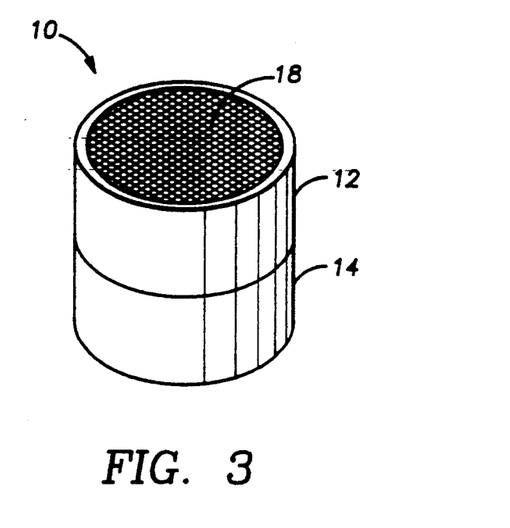
FIG. 3 is a perspective view of an embodiment of the wafer of the present invention in its assembled state.

The wafer 10 is shown in its assembled state in FIGS. 2 and 3. To assemble the wafer, the porous membrane 20 is placed onto the lower retaining ring 14 such that the edges of the membrane extend past the ring around its entire outer circumference. The housing ring 16 is then placed on the lower membrane 20 and pushed into the lower retaining ring 14. The diameters of rings 12, 14 and 16 are selected, with the membrane, to form a fluid tight seal between the rings. After placement of solid phase support material into the housing ring, the upper membrane 18, retaining ring 12 and housing ring 16 are similarly sealed by placing membrane 18 over ring 16 and pushing ring 12 into place. In addition to creation of the fluid tight seal, the design facilitates the retention of the membranes firmly in place during the chemical reaction. This result is achieved by overlapping the edges of the membranes over the housing ring 16 and anchoring the membranes between the retaining rings 12 and 14 and housing ring 16. As FIGS. 2 and 3 illustrate, in the assembled wafer 10, the membranes 18 and 20 extend across the ends of the inner housing ring 16, with the ends of the membrane held between the outer retaining rings 12 and 14 and the inner housing ring 16.

The assembled wafer contains the reactant components 22. The reactant components are solid phase supports which have been derivatized by covalently linking a residue, e.g., nucleoside, to the solid support via an organic spacer arm.

The residue, or first base, from which polymeric growth will begin, is thus separated from the surface of the support material. The reactant components 22 are placed in the inner housing ring 16 prior to sealing the wafer with membrane 18 and retaining ring 12. Thus, the housing ring 16 and membranes 18 and 20 together form a reaction chamber for the reactant components 22.

As previously noted, the above disclosure is directed to one particular wafer design. It is emphasized that numerous wafer designs are possible and within the scope of the present invention. For example, the wafer could include a snap-together or screw-together design. In particular, an alternative embodiment of wafer 10, could have rigid porous frits, snapped into indentations in the inside surface of the housing ring near its upper and lower edge.

The wafer is a rigid, chemically inert chamber so that it will not interfere with or react with the chemicals used in the synthesis of the biopolymers. The outer retaining rings and inner housing ring can be fabricated from a variety of inert materials, for example, TEFLON and other fluorocarbons, such as KEVLAR and KALREZ.

The size of the wafers can vary over a wide range. For synthesis of milligram quantities of polynucleotides, the inner diameter of the inner retaining ring is preferably in the range of about 2-10 mm, and the height is from about 2-10 mm. For gram quantities of product, the inner diameter is preferably from about 20-100 mm and the height is from about 20-100 mm. Furthermore, the height of the column of stacked wafers can be increased to permit simultaneous synthesis of larger numbers of different polynucleotide chains. One skilled in the art will recognize, of course, that the size of the wafers may be smaller or larger than the above dimensions depending upon the specifics of the particular synthesis. Furthermore, one skilled in the art will recognize that the column dimensions will change depending on the biopolymer to be synthesized and the solid phase support used. In the production of peptides, the wafer dimensions will generally tend toward the upper limits of these ranges.

The porous materials which allow for the flow of reagents through the wafers are also formed from a chemically inert material. For example, suggested inert materials include TEFLON and other fluorocarbon materials, such as KEVLAR, fritted or scintered glass, and titanium and stainless steel frits. Pore size can vary, but is selected so as to allow sufficient flow of the reagents and washing solutions through the wafer, while retaining the support material and growing biopolymer chains within the wafers. A pore size of 50–100 micrometers is suggested for use with CPG supports, which are typically 120–180 micrometers in diameter. The porous material can assume a variety of designs as long as the necessary flow and containment are achieved. As illustrated and described herein, the porous material can be in the form of a flexible membrane, a rigid fritted structure, etc.

The solid phase support on which the biopolymer chain is formed can be selected from the variety of known supports. Suggested supports for polynucleotide synthesis include polystyrene-divinyl-benzene (DVB), polyamide-Kieselguhr, silica, controlled pore glass (CPG) and plastic resins such as MONOBEADS (a resin produced by Pharmacia). CPG, silica and MONOBEADS are particularly preferred as the solid phase support since they are rigid, i.e., do not swell or contract. Suggested supports for polypeptide synthesis include polystyrene and vinylbenzene resins, polyamide resins, polyamide-Kieselguhr resins, benzhydrylamine resins, and macroreticular resins.

Support materials of large pore size, for example 200–2000 Å, permit good accessibility by the reagents to the growing chain and efficient washing away of reactants. Also, these supports permit assembly of relatively long chains, e.g., 50–200 residues, without steric hindrance between polymers.

The amount of the support material 22 supplied to the wafer can vary. Factors to be considered in determining the amount of support material added include the amount of DNA, RNA, polypeptide, polysaccharide or other biopolymer needed, flowrate and the extent of derivitization of the solid phase support, e.g., micromoles monomeric residue per gram of support. Advantageous results are achieved where the wafers are from two-thirds to three-fourths full, thus allowing for mixing and any possible swelling. The use of rigid solid phase supports of very large pore size, e.g., silica of 3000–4000 Å, permits superior mass transfer within the supports, such that wafers can be completely filled with derivatized supports.

Figure 4:
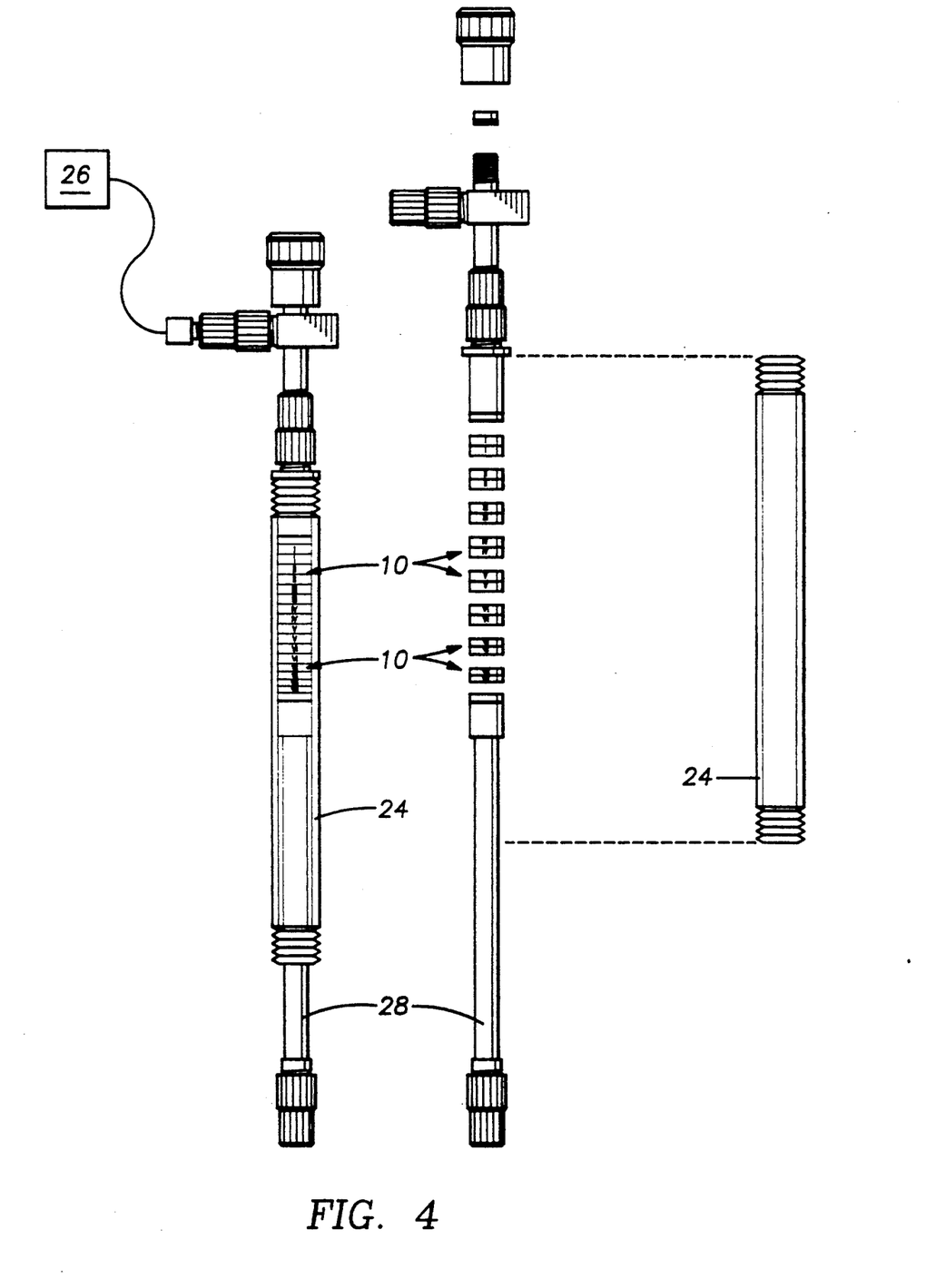
FIG. 4 is a schematic view of a column assembly of the segmented wafer synthesis device according to the present invention.
Figure 5:
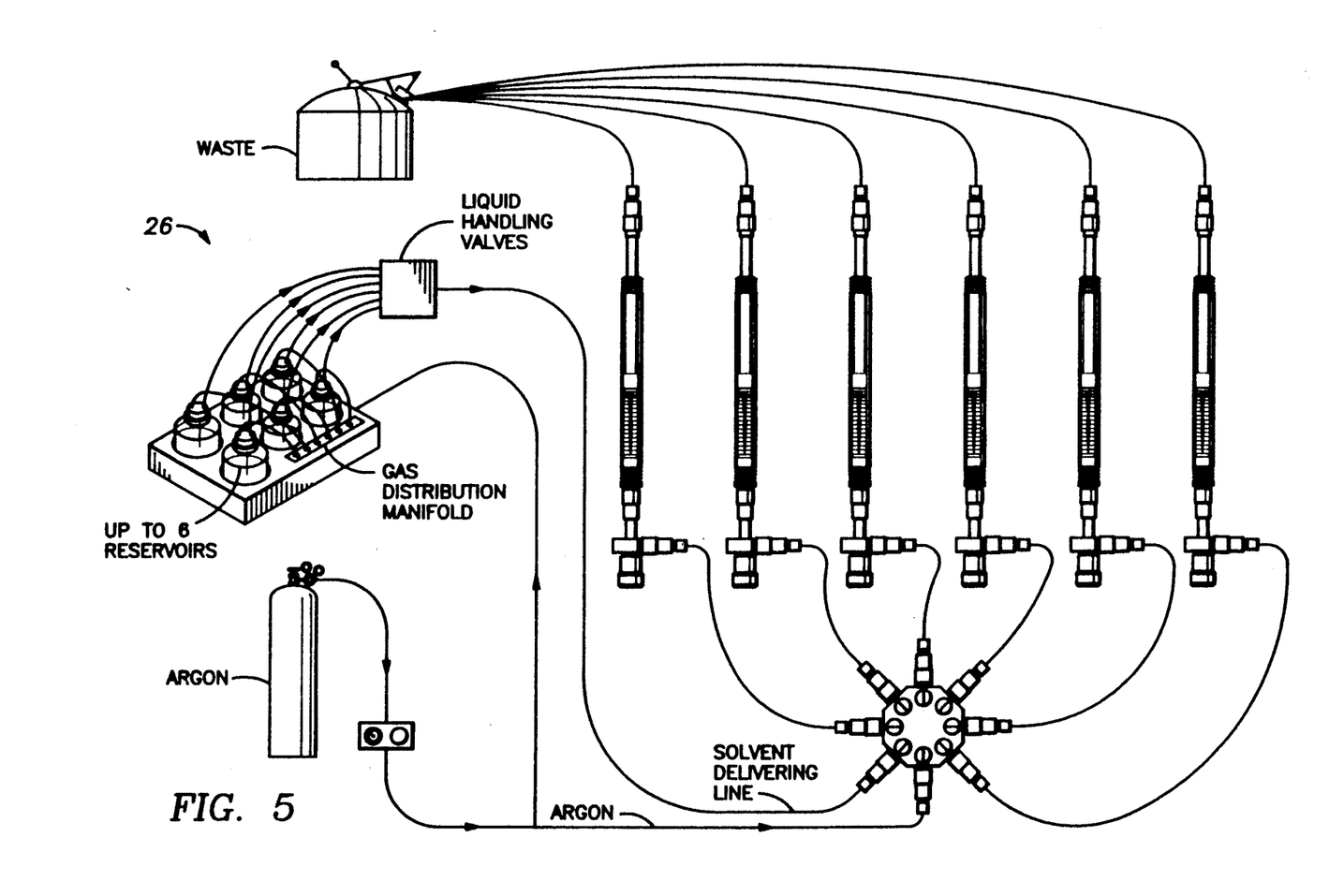
FIG. 5 is a schematic view of a segmented wafer synthesis device according to the present invention.

With reference to FIG. 4, once assembled the wafer is placed in a column 24 through which reagents and washing solvents are passed to create a reaction cycle. The column 24 is designed to receive a number of wafers 10. As illustrated in FIGS. 4 and 5, delivery system 26 utilizing, for example, argon pressure, passes the reagents and washing solution through the column 24 and wafers 10. Preferably, the flow passes upwardly through the column to facilitate the reaction by causing mixing and distribution of the porous support material within a given wafer. Typically, the delivery system is connected to at least four columns in parallel corresponding to the four bases, cystosine (C), thymine (T), guanine (G) and adenine (A). Additional columns can be provided if modified bases or mixtures of bases are to be utilized in the synthesis. Any number of wafers can be placed in each column depending on the number of biopolymer sequences to be produced. For example, it is possible to place just one wafer in a column. However, this is typically costly and inefficient and, as pointed out earlier, is one problem with some of the presently available designs. Typically, the number of wafers may be in the order of 15–25 per column. However, fewer wafers or more wafers can be utilized. The number of wafers selected must, of course, allow for sufficient flow through the column. In this regard, the outer diameters of the wafers should be selected to provide a snug fit with the inner column surface to force flow through the wafers themselves, and not along the sides of the column. If additional flowrate is required, a different solvent delivery system may be utilized. Also, the number of wafers, of course, will vary with varying column heights.

Figure 10:
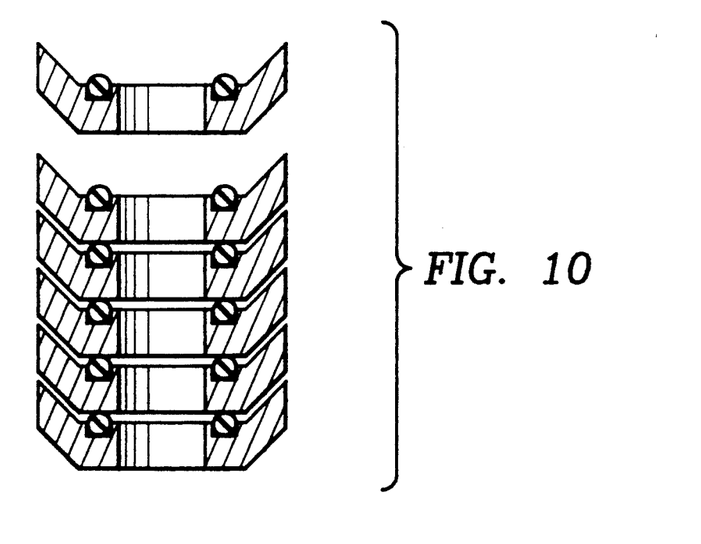
FIG. 10 is a cross-sectional view of another embodiment of the wafer and snapper.

The column 24 can be manufactured from any inert material. For example, glass and stainless steel are two preferred materials. The column typically includes a plunger 28, which allows for variable numbers and heights of wafers within the column. An example is shown in cross-section in FIG. 10. In this alternate embodiment of the wafer 10 and column design 24, the wafer 10 fits into the center of the snapper 11. The snappers are then compressed on a seal 25 using an air piston to form a fluid tight seal. The combination of the snapper and wafer fit form a column 24 for the synthesis.

In a further embodiment, the wafers can snap together to form, by themselves, a segmented wafer column, thereby obviating the need for a separate supporting column. In this embodiment, the delivery system 26 would be connected directly to the segmented wafer column.

In the synthesis, as previously noted, a series of columns are set up containing the wafers. Each column is provided with a reagent for residue addition. For example, in the synthesis of DNA, one column will be for the addition of cystosine (C), another for thymine (T), another for guanine (G), and another for adenine (A). Similarly for RNA synthesis, the thymine can be replaced with the reagent necessary for adding uracil (U). As previously noted, however, the number of columns used is not essential to the present invention. A single column will suffice, but this increases the time required for completion of the biopolymer synthesis. Reagents must be switched for each synthesis and fewer samples can be synthesized in one column than in four columns. Thus, use of multiple columns facilitates the number of reactions to be carried out and increases the efficiency of the procedure. A further method involves the addition of dimers, trimers, etc. In this synthesis additional columns are added. For example, with a dimer one would use 20 columns, i.e., one column for each dimer which can be added and one column for each single nucleoside base to be added.

Returning to the DNA method, wafers are selectively positioned in one of the T, G, C, or A columns, depending on the first base to be added. After the appropriate passage of the reagents and chemicals for the addition of that base to the polynucleotide chain (constituting a reaction cycle), the wafers are removed from that column, sorted for the next synthesis step, inserted into the appropriate column and the synthesis step repeated. This procedure is repeated until the desired polynucleotide sequences are synthesized. Thus, with the use of different columns for base addition, each wafer goes through its individual pattern of synthesis. This procedure allows for the concurrent synthesis of many different polynucleotides.

The present invention can be used for the production of any biopolymer by solid phase synthesis. Particularly preferred syntheses include the synthesis of polynucleotides, polypeptides and polysaccharides by solid phase methods, provided that these methods employ a flow-through design, as implemented in the present invention. A particularly preferred solid phase route for peptide synthesis using the present invention is the previously mentioned Fmoc pentafluorophenyl ester method, utilizing polyamide-Kieselguhr supports.

The procedure is applicable to the simultaneous synthesis of multiple defined-sequence biopolymers by manual, semi-automated or fully automated procedures. For example, a semi-automated machine can be utilized that is controlled by a microcomputer. A program editor permits the operator to control the delivery of all reagents to the solid phase supports. The computer also can provide the operator, at each step, with instructions for sorting the wafers and placing them in the correct column. In the semi-automated system, the operator performs these latter functions. Of course, one skilled in the art recognizes that the fully automated system is preferred. In this system sorting of the wafers and their subsequent placement in the next column is performed by a machine.

The segmented wafer device is designed specifically for biopolymer syntheses that can be achieved by solid phase, flowthrough methods. The advantage of solid phase chemistry in the synthesis of biopolymers is that the step-wise addition to form a biopolymer is greatly facilitated because the product does not have to be purified after each condensation step. Reactants and reagents can simply be washed away. This solid phase synthetic approach has been developed for a number of different chemistries used in biopolymers synthesis. The segmented wafer can be used with all these methods.

In the synthesis of polynucleotides, the efficiency of the reaction in each step of solid phase synthesis has been measured to be between about 95 and greater than 99%, with the cycle time of approximately 5–30 minutes per nucleoside added. This approach is preferred when the quantity of desired product is in the milligram range, which is ample for most applications. In addition, solid phase synthesis is highly preferred for synthesis of mixed probe polynucleotides in which a mixture of residues exists at certain positions in the sequence.

The phosphoramidite method of solid phase synthesis (FIG. 9) is preferred for use with the present invention. In this approach the activated intermediate is a 5'-DMT-2'-deoxynucleoside 3'-phosphoramidite. The method begins with covalent linkage of the 3'-hydroxyl group of the first nucleoside to the solid support via a long chain alkyl spacer arm.

Figure 9A:
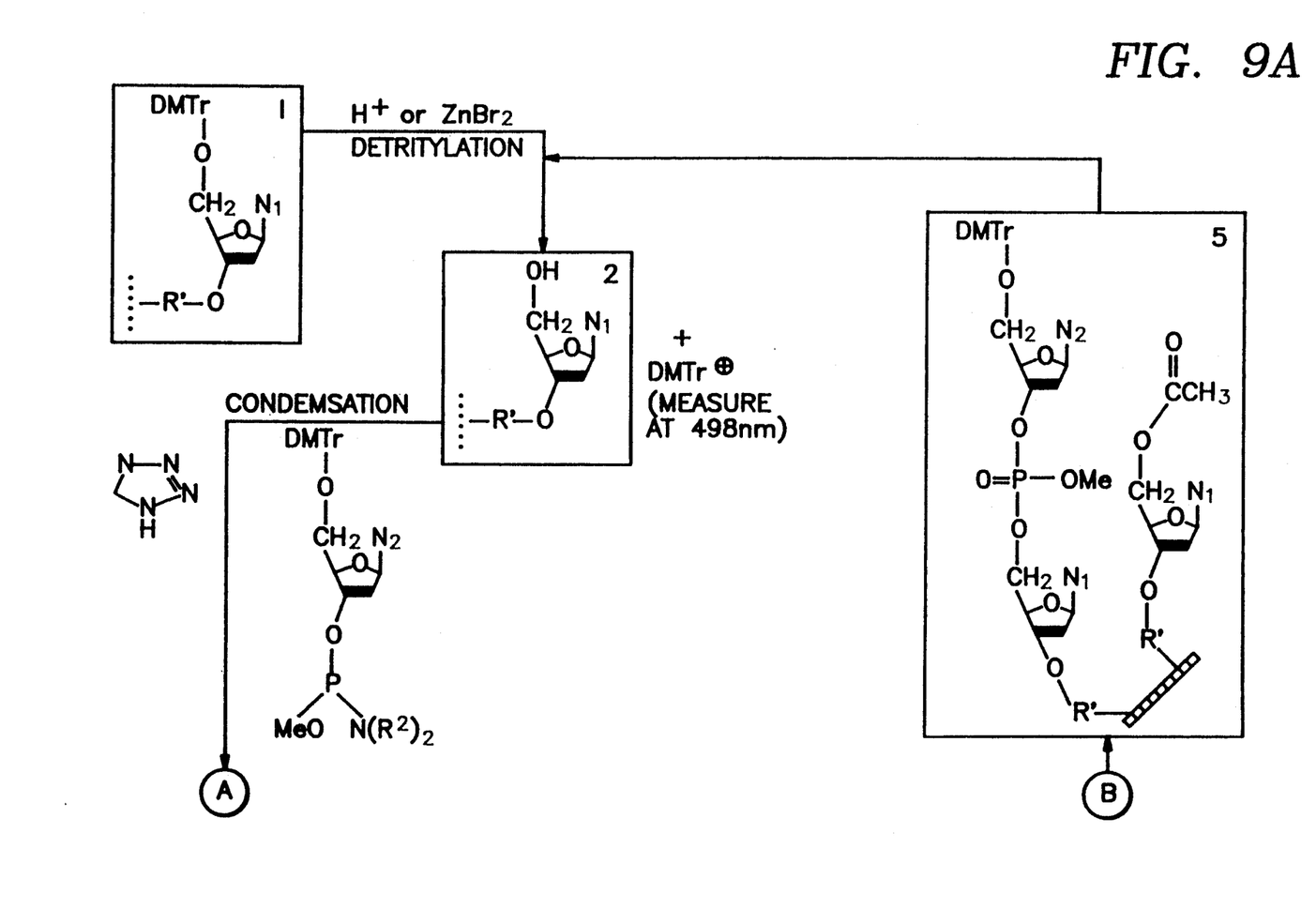
FIG. 9 is the phosphoramidite method of solid phase synthesis.
Figure 9B:
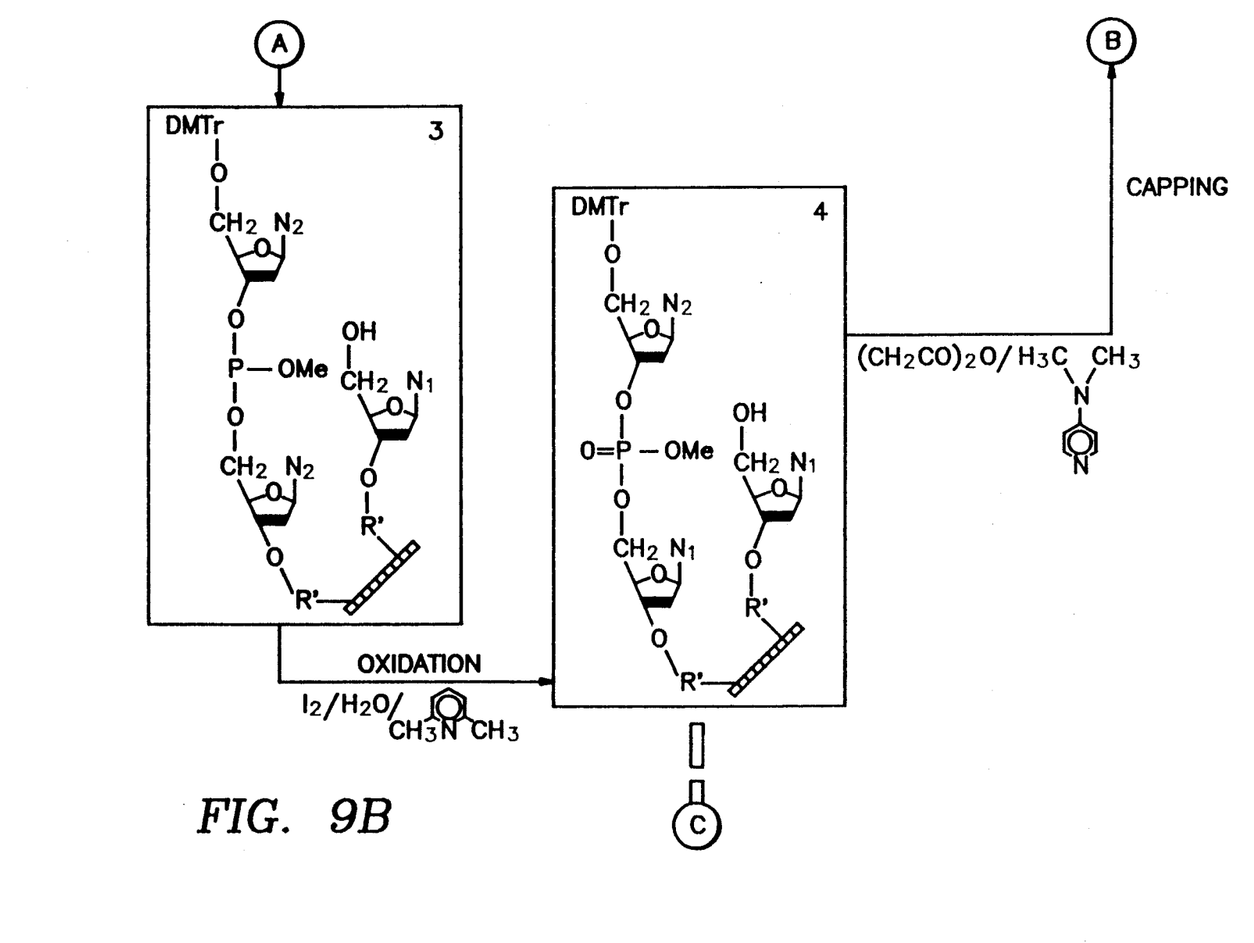
Figure 9C:
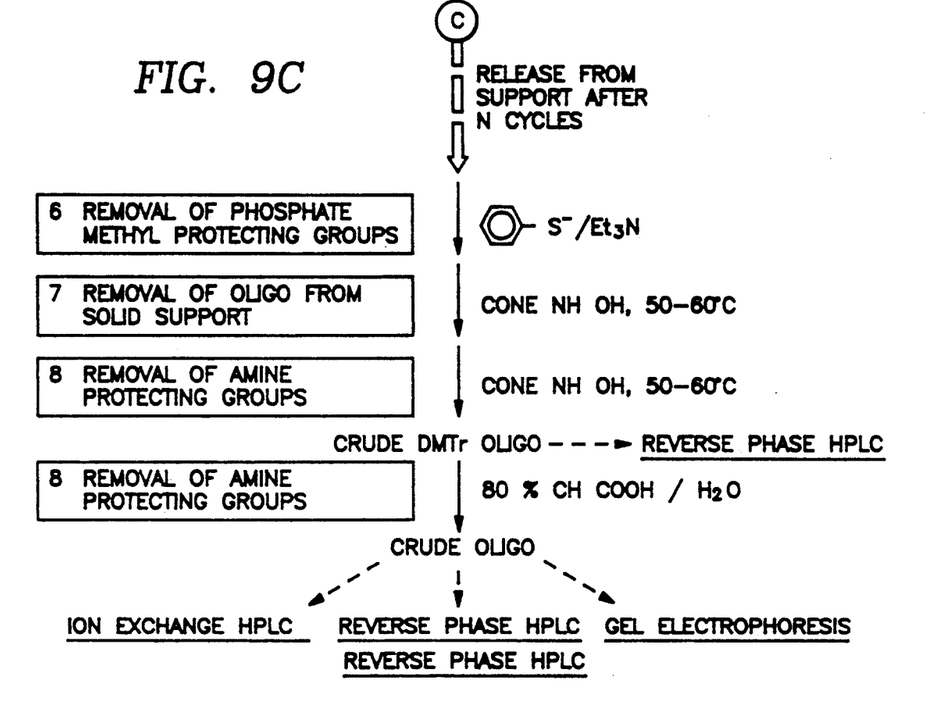

The acid-labile dimethoxytrityl group (DMTr) is cleaved from the 5'-OH of the support-bound nucleoside by treatment with dilute dichloroacetic acid. Nucleoside phosphoramidites (at 10–20 fold molar excess over support-bound nucleoside 5'-OH) are activated by protonation of their nitrogen atom using tetrazole under anhydrous conditions, and condensation occurs as shown in step 2. At the completion of each successive coupling, the reactive phosphite is converted to a more stable phosphate using a solution of iodine in tetrahydrofuran and water (step 4). If desired, a "capping" reaction can next be carried out with acetic anhydride/-dimethylaminopyridine/lutidine, (step 5) to acetylate the 5'-hydroxyl groups that did not react with the activated phosphoramidite in the previous coupling, to prevent propogation of "truncated" and "nonsense" (jumbled) sequences.

At the end of each synthesis cycle, the exocyclic amino groups of A, C and G remain amide protected, the internucleotide phosphate groups are methyl esterified, and the 3'-OH end of the growing chain remains succinate-linked to the support. Prior to addition of the next residue, the detritylation step is repeated. The brilliant orange DMTr cation can be quantitated spectrophotometrically to calculate a coupling efficiency. Using the segmented wafer method, coupling efficiencies in the range of about 95–99% can be achieved.

At the end of the synthesis, the phosphate methyl protecting groups are cleaved by thiophenoxide ion, which forms from thiophenol in the presence of triethylamine (step 6). This step is not required if 2-cyanoethyl phosphoramidites are used in the synthesis. Then the alkali-labile acyl groups (protecting the ezocyclic amino groups of A, G and C), cyanoethyl groups (if used to protect phosphates) and covalent linkage to the solid support are cleaved by treatment with aqueous ammonium (steps 7 and 8). If the DMTr group remains, it is cleaved by concentrated acetic acid (step 9).

As discussed previously, another method (the phosphotriester method) is commonly used for polynucleotide synthesis. Although the phosphotriester method could be adapted for use with the present invention, it is less preferred because of longer cycle times and greater requirement of anhydrous conditions which are difficult to maintain during sorting of wafers.

The previously mentioned recent developments in solid phase polynucleotide synthesis, including in situ phosphoramidite production, amidine protecting groups and ribopolymer synthesis, could be used in the present invention. Furthermore, it would be obvious to one skilled in the art to apply the present invention to future developments in biopolymer synthetic chemistry, including improvements in condensation, protection and deprotection reactions or in solid phase supports.

Use of the above synthetic methods in the segmented wafer synthesis of biopolymers can be automated using commercially available systems. For example, an automated machine containing four columns, Cruachem model PS200 synthesizer, can be controlled by an IBM PC-compatible microcomputer. The program editor permits the operator to control the delivery of all reagents to the solid phase support. This is required for the development of the reaction cycle to be used in the segmented wafer method. Furthermore, the computer can facilitate the sorting process by keeping track of the order of the wafer insertions into the columns. A computer program is utilized to direct the placement of each wafer in the appropriate columns during the synthesis. Thus, a printout indicates which wafers (identified by numbers) are to be placed into a given column after each reaction cycle, so that wafers are easily sorted and the separate wafers put in columns for the appropriate synthetic reaction sequence. The use of the computer program decreases the amount of error and increases the reliability of the synthesis. Additionally, development of an automated sorting machine, which is also controlled by the computer and interfaced with the existing synthesizer, is possible, to provide for completely automated synthesis of biopolymers using the segmented wafer device.

The present invention is further described by way of the following examples.

EXAMPLE I

This example describes the standard procedure used for segmented synthesis of polynucleotides within chemically inert porous wafers. Details of specific applications of this procedure are given in subsequent examples.

A. Operation of Interactive Synthesis Setup Program.

DNA sequences to be synthesized are entered (5'-3'direction) using a word processing program on an IBM compatible computer. The sequence files are stored in a non-document file and named in the format. Once the sequences are entered, the Wafer-DNA Setup Program (written in Basic) is run with the sequence files in the disk drive. The Wafer-DNA Program examines the sequence files and generates a hard copy of the following information: (i) a listing of all sequences entered, along with identifying numbers and names assigned for each, (ii) a listing of numbered wafers to be loaded with each type of derivatized CPG support (defining the 3'-terminal base in each sequence), and (iii) a schematic for directing the sorting of wafers after each reaction cycle.

B. Reagent Preparation, Wafer Assembly and Set-up of Cruachem Model PS200 DNA Synthesizer Using the software provided with the Cruachem DNA synthesizer, a method called "Wafer-CE20" has been created. The method is as follows:

| Method: | wafer-ce20 |
|---|---|
| Reservoir 1: | Acetonitrile |
| Reservoir 2: | DMAP/THF |
| Reservoir 3: | Acetic Anhydride/THF/Lutidine |
| Reservoir 4: | Iodine/THF/Lutidine/Water |
| Reservoir 5: | Acetonitrile |
| Reservoir 6: | DCA/DCE |
| Method: | wafer-ce20 |

First Cycle
Step 1:   Wash Acetonitrile Fixed
          Duration = 2:15 Minutes
Step 2:   Deblock DCA/DCE Base Variable
          A              duration = 1:30 Minutes
          G              duration = 1:30 Minutes
          C              duration = 2:30 Minutes
          T              duration = 2:30 Minutes
          Purine (A/G)   duration = 2:30 Minutes
          Pyrimidine (T/C) duration = 2:30 Minutes
          N (A/C/G/T)    duration = 2:30 Minutes
Step 3:   Wash Acetonitrile Fixed
          Duration = 1:30 Minutes Normal Cycle
Step 1:   Reaction Fixed
          Duration = 4:00 Minutes
Step 2:   Wash Acetonitrile Fixed
          Duration = 1:30 Minutes
Step 3:   Wash Acetic Anhydride/THF/Lutidine Fixed
          Duration = 0:12 Minutes
Step 4:   Wash DMAP/THF Fixed
          Duration = 0:12 Minutes
Step 5:   Wash Acetic Anhydride/THF/Lutidine Fixed

|  |  |
|---|---|
| Step 6: | Wash DMAP/THF Fixed |
|  | Duration = 0:12 Minutes |
| Step 7: | Wash Acetic Anhydride/THF/Lutidine Fixed |
|  | Duration = 0:12 Minutes |
| Step 8: | Wash DMAP/THF Fixed |
|  | Duration = 0:12 Minutes |
| Step 9: | Wash Acetic Anhydride/THF/Lutidine Fixed |
|  | Duration = 0:12 Minutes |
| Step 10: | Wash Acetonitrile Fixed |
|  | Duration = 0:12 Minutes |
| Step 11: | Cap/functionalize Fixed |
|  | Duration = 1:30 Minutes |
| Step 12: | Wash Acetonitrile Fixed |
|  | Duration = 1:30 Minutes |
| Step 13: | Wash Iodine/THF/Lutidine/Water Fixed |
|  | Duration = 2:00 Minutes |
| Step 14: | Wash Acetonitrile Fixed |
|  | Duration = 1:30 Minutes |
| Step 15: | Cap/functionalize Fixed |
|  | Duration = 60:00 Minutes |
| Step 16: | Deblock DCA/DCE Base Variable |
|  | A       duration = 1:30 Minutes |
|  | G       duration = 1:30 Minutes |
|  | C       duration = 2:30 Minutes |
|  | T       duration = 2:30 Minutes |
|  | Purine (A/G)     duration = 1:30 Minutes |
|  | Pyrimidine (T/C) duration = 2:30 Minutes |
|  | N (A/C/G/T)      duration = 2:30 Minutes |
| Step 17: | Wash Acetonitrile Fixed |
|  | Duration = 1:30 Minutes |
| Final Cycle |  |
| Step 1: | Reaction Fixed |
|  | Duration = 4:00 Minutes |
| Step 2: | Wash Acetonitrile Fixed |
|  | Duration = 1:30 Minutes |
| Step 3: | Wash Iodine/THF/Lutidine/Water Fixed |
|  | Duration = 2:00 Minutes |
| Step 4: | Wash Acetonitrile Fixed |
|  | Duration = 4:00 Minutes |

Before synthesis begins it is necessary to assemble the wafers. For each wafer, the bottom portion of the wafer is assembled first so that the derivatized controlled pore glass (CPG) support material can be added through the top. Approximately 18 mg of the appropriate CPG is added, as directed by the printout from the Wafer-DNA Setup Program. Finally the wafer is closed by placing another piece of the porous TEFLON cloth over the reaction chamber and securely fastening this with the outer TEFLON retaining ring. The wafers are loaded into the appropriate columns, as directed in step 2 of the printout from the Wafer-DNA Setup Program.

To prepare the synthesizer for operation, the reservoirs are filled with their respective reagents and the solvent lines are flushed, using the operating program supplied with the Cruachem synthesizer. The last reagents to be prepared are the phosphoramidites and the sublimed tetrazole. Table I describes the reagents used for polynucleotide synthesis by the segmented wafer method.

|  |  |
|---|---|
| NORMAL CYCLE: | Wafer - CE20 Method |
| SOLVENTS/REAGENTS PER COLUMN OF 10 WAFERS | |
| 1. Acetonitrile - 12.5 ml (with solvent organizer stand, use 1l reservoir) | |
| 2. 6.5% Dimethylaminopyridine in THF (w/v) 1.2 ml | |
| 3. Acetic anhydride/THF/Lutidine - 1.6 ml | |
| 4. Iodine (0.1M in water/lutidine/THF - 1:10:4) - 4 ml | |
| 5. 3% Dichloroacetic acid/dichloroethane (w/v) - 4 ml | |
| SOLVENT FLOW RATE: | 2 ml/min |
| AVERAGE CYCLE TIME: | 18 min |
| SYNTHESIS SCALE: | 0.5-1 micromole per wafer |
| SUPPORT: | Nucleoside-CPG, typically 15-20 mg per wafer |
| MONOMER SOLUTION: | 0.1M CE phosphoramidite |
| 6.67 ml acetonitrile/.5 g T-phosphoramidite | |
| 6.00 ml acetonitrile/0.5 g G-phosphoramidite | |
| 5.80 ml acetonitrile/0.5 g A-phosphoramidite | |
| 6.00 ml acetonitrile/0.5 g C-phosphoramidite | |
| Catalyst - 0.5M tetrazole (20 ml acetonitrile/0.7 g tetrazole) | |
| Mix 0.5 ml monomer and 0.5 ml catalyst and inject into the column. | |

C. Synthesis of Polynucleotides.

Using the PS200 Cruachem DNA Synthesizer and resident operating software, the Wafer-CE20 method and the segmented wafer synthesis device depicted in FIG. 5, the segmented synthesis of polynucleotides is carried out, employing the previously described 2-cyanoethyl phosphoramidite chemistry. After the wafer-containing columns are connected to the synthesizer, the first cycle, consisting only of detritylation and washing, is carried out as indicted in the method ("First Cycle," Steps 1 through 3). Initiation of each subsequent cycle occurs upon injection of phosphoramidites, immediately preceding Step 1 ("Normal Cycle"). Step 15 ("Normal Cycle") is not a repeat of capping Step 11, but rather is a variable "pause" period during which the wafers are sorted, as directed by the printout from the Wafer-DNA Setup Program. In each normal cycle, as soon as sorting of wafers is completed and columns are reconnected to the synthesizer, the synthesis cycle is resumed and detritylation and washing are carried out. The final cycle is identical to the normal cycle, except that capping and detritylation are omitted. If desired, after synthesis within all wafers is complete, the wafers can be reassembled into columns and subjected to detritylation to remove the remaining 5'-DMT protecting groups.

After the synthesis has been completed, the wafer contents are emptied into screw-top vials and the DNA is cleaved from the support, further deblocked and purified by prior-art procedures, following the instructions provided in the Cruachem PS200 operation manual.

The above procedure has been carried out numerous times, resulting in the simultaneous synthesis (at a scale of 0.5-1.0 micromole) of between 3 and 79 different DNA sequences in a single day, of length ranging from 15 to 25 residues. The coupling efficiency at each step was typically about 95% and DNA sequences have been confirmed by the Maxam-Gilbert sequencing method.

EXAMPLE II

Simultaneous Synthesis of Three Test Polynucleotides

To assess the usefulness of the segmented wafer synthesis device for biopolymer synthesis, simultaneous synthesis of three pentadecamers was carried out, using the equipment illustrated in FIGS. 1-5 and the general procedure described in Example 1, as further detailed below. The nucleotide sequences of the test DNA molecules were:

1. 5'-GAGCCATCAAGCCAG-3'
2. 5'-GCTGCAGAGAGGCCA-3'
3. 5'-GAGGTGTTGGAGCTG-3'

The details of the synthesis are:
SOURCE OF REAGENTS: Cruachem

SCALE OF SYNTHESIS AND WAFER DIMENSIONS: Each wafer (10 mm o.d. × 4 mm h.) contained 18 mg of nucleoside-CPG (approximately 0.6 micromole) and was assembled from components of the following dimensions (see FIGS. 1-3): Porous Teflon cloth, 12 mm diameter; Inner housing ring, 4 mm i.d. × 4 mm h.; Outer retaining rings, 10 mm o.d. × 2 mm h.; Internal volume, 0.050 ml.

REACTION CYCLE AND REAGENT/SOLVENT USAGE: The standard "CE Phosphoramidite" protocol and reaction cycle, as specified in the Cruachem PS200 Synthesizer instruction manual for prior-art operation, was used in this experiment. The "standing" steps of the reaction cycle (condensation step 1 and capping step 11) were carried out for the same times given in Example I for the "wafer-CE20" method (4.0 and 1.5 minutes, respectively). Step 1 was initiated by mixing 0.1 ml of 0.1M CE phosphoramidite and 0.1 ml of 0.5M tetrazole (both in anhydrous acetonitrile) in a syringe and injecting the mixture into each column. The remaining "flow" steps in the reaction cycle were carried out (at 2 ml/min) for one-half the time specified in Example I for the "normal cycle" of the "wafer-CE20" method. The columns were briefly flushed with Argon just prior to the sorting step 15. The average cycle time was 11 minutes. The quantity of reagents consumed per cycle per wafer, along with approximate cost per base addition (based on catalog price of nucleoside-CPG, reagents and solvents) were as follows:

3.7 ml acetonitrile
  0.4 ml 6.5% dimethylaminopyridine in THF
  0.5 ml acetic anhydride/THF/Lutidine
  1.2 ml iodine (0.1M in water/lutidine/THF-1:10:4)
  1.2 ml 6.3% dichloroacetic acid/dichloroethane
  0.06 ml 0.5M tetrazole in acetonitrile
  0.06 ml 0.1M 2-cyanoethyl phosphoramitite in acetonitrile Cost per base addition: $1.98, compared with $5.42/base if synthesis were carried out by the Cruachem PS200 Synthesizer, operated in the standard (prior-art) mode.

Figure 6:
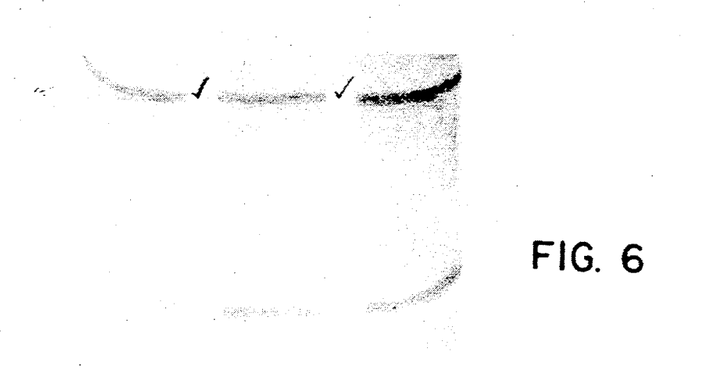
FIGS. 6, 7 and 8 are photographs illustrating the UV shadowing visualization of DNA produced by the present invention.

POST-SYNTHESIS DEPROTECTION, DNA PURIFICATION, ANALYSIS: The final detritylation step was carried out on the column (as in step 16 of the "normal cycle"). After wafer contents were emptied into 1.5 ml eppendorf tubes, 1 ml of fresh concentrated ammonium hydroxide was added, tubes were capped and mixed. After 20 minutes at room temperature (during which cleavage of polynucleotides from the CPG occurred), the liquid, along with 1 ml additional concentrated ammonium hydroxide, was transferred to a screw-top glass vial (15 ml o.d. × 45 mm height), tightly sealed with a Teflon-lined cap, and incubated at 55 degrees C for 6-15 hours (to deprotect exocyclic amino groups of C, A and G). The ammonia was removed by vacuum, using a Savant SpeedVac concentrator (1 hr by water jet, followed by overnight at high vacuum). The dried DNA was dissolved in a small volume of water, then purified by electrophoresis (20% polyacrylamide, 7M urea). Visualization by "UV-shadow" gels produced from 20 $A_{260}$ units of the crude reaction products is represented by FIG. 6.

The uppermost band in each gel represents the desired full-length product, the faint lower bands represent "failure" sequences, and the dark band at the bottom represents the bromophenol blue marker dye. These gels were comparable to those obtained with similar DNA products produced on an automated Applied Biosystems Model 380A Synthesizer (using prior-art phosphoramidite procedure) and during which coupling efficiencies were measured (by the standard trityl release assay) to be 98-99%. Thus, the average coupling efficiency in the synthesis of the three pentadecamers by the segmented wafer synthesis device was estimated to be about 98-99%.

COMMENTS: These DNA products were successfully 5'-phosphorylated (using T4 polynucleotide kinase) and used as hybridization probes, by prior-art procedures. The high yield, quality and reduced cost of the product demonstrates the usefulness of the present invention for simultaneous polynucleotide synthesis. Furthermore, an important finding is that the manual sorting process carried out after each reaction cycle does not negatively affect the synthesis.

EXAMPLE III

Simultaneous Synthesis of 62 Biopolymers

To assess the utility of the present invention for simultaneous synthesis of large numbers of biopolymers, 62 different DNA nonadecamers were synthesized, using the equipment illustrated in FIGS. 1-5 and the general procedure outlined in Example I, as further detailed below. The nucleotide sequences of the test DNA molecules were:

1. 5'-GAAAGGTTAGATTCCTCAC-3'
2. 5'-AAGAAAGGTCAAATTCCTC-3'
3. 5'-TGGTGGAAGCAAGGTTAAA-3'
4. 5'-GCTTGGTGGCAGAAAGGTT-3'
5. 5'-GAATGGTTTCTAACTGCTT-3'
6. 5'-TTTTCAAAGCGAATGGTTT-3'
7. 5'-GGTTTAATGTCCTGTTTTT-3'
8. 5'-GGCGTTTTCATCAGCGGTT-3'
9. 5'-CCACCCGGCCTTTTCTTCA-3'
10. 5'-GACGGCGCGTCACCCGGCC-3'
11. 5'-GTTGACGGCTCGCCACCCG-3'
12. 5'-TCTTCCAGTTCCTCTTCCG-3'
13. 5'-AGTTCTTCCCGTACCTCTT-3'
14. 5'-CCAGACCACCATACTCCAG-3'
15. 5'-GATTTCAGCATCGCCAGAC-3'
16. 5'-AGCGGCAGCATGTCGGTGT-3'
17. 5'-TGCACACGCTCGGTTTTCG-3'
18. 5'-TATGCACACCCCGGTTTT-3'
19. 5'-AAGAGGTATCCACACGCCC-3'
20. 5'-GGTGATAAGCGGTATGCAC-3'
21. 5'-CAACGTCCCCTTGCAGTTA-3'
22. 5'-ATAAACGTCTCGTTGCAGT-3'
23. 5'-ACGATAAACCTCCCGTTGC-3'
24. 5'-TTTGCAGGTCAGGATCGGT-3'
25. 5'-ATCTTTTGCCGGTTAGGAT-3'
26. 5'-CGCACCGGACTGTTTTGCA-3'
27. 5'-TCGTTACGCTCCGGAATGT-3'
28. 5'-CTTCGTTACCCACCGGAAT-3'
29. 5'-TACGACGACGTTCTTCGTT-3'
30. 5'-ACGCCTGGCCGATACGACG-3'
31. 5'-GCAATAAACTCCTGGCGGA-3'
32. 5'-GGCGCAATAGACGCCTGGC-3'
33. 5'-TCCTCTGGCTCAATAAACG-3'
34. 5'-CAATCTGCGCGTAGTCCGC-3'
35. 5'-ATAATGCGCCGTTCAATCT-3'
36. 5'-CCATAATGCCCAGTTCAAT-3'
37. 5'-GAAAGATGCTCCATAATGC-3'
38. 5'-GAAAGATGCTCCATAATGC-3'
39. 5'-GCGAAAGATCCGCCATAAT-3'
40. 5'-CGCTACGGCCTTGCTCGCT-3'
41. 5'-ATCGCTTTCTCGCTACGGC-3'
42. 5'-TGATCGCTTCCGCGCTACG-3'
43. 5'-AAATCAGACGAAAGTTGAT-3'
44. 5'-TCATGCCATCAATCAGACC-3'
45. 5'-CACTCATGCGATAAATCAG-3'
46. 5'-GAGCACGGGCGCGTTCCAT-3'
47. 5'-TTCGCCTGATCACGGGTGC-3'
48. 5'-TGCTCTTTCTCCTGAGCAC-3'
49. 5'-CGTCCGTCCCGCGTTTCAA-3'
50. 5'-GACGGCGTCTGTCCAGCGT-3'

-continued
51. 5'-ACAGACGGCCTCCGTCCAG-3'
52. 5'-GATACAGACCGCGTCCGTC-3'
53. 5'-TTAATGGCTTCACGTTCAG-3'
54. 5'-GCGTTAATGTCTGCACGTT-3'
55. 5'-TTGGCGCGTCAATGGCTGC-3'
56. 5'-CGGTTCCCTCCATTGGCGC-3'
57. 5'-ATGTCGGCGTCGGTTCCCT-3'
58. 5'-CGTTTGATACTGTCGGCGG-3'
59. 5'-TCGCCCGTTCGATAATGTC-3'
60. 5'-TCAACGGCACTCATCGCCC-3'
61. 5'-TCATCGTGTTCCTGCATGA-3'
62. 5'-GTTCATCGTCTACCTGCAT-3'

The details of the synthesis are:

SOURCE OF REAGENTS: Cruachem

SCALE OF SYNTHESIS AND WAFER DIMENSIONS: As in Example II, 18 mg of derivatized CPG (approximately 0.6 micromole) was placed into each wafer of dimensions, 10 mm o.d. ×4 mm height.

REACTION CYCLE: The synthesis was carried out using the "wafer-ce20" method (reaction cycle as listed in Example 1). A mixture of 0.5 ml 0.5M tetrazole and 0.5 ml 0.1M 2-cyanoethyl phosphoramidite was injected upwards through the column of wafers to initiate step 1. Duration of average reaction cycle was 18 minutes. Average time required for sorting (step 15) was 12 minutes.

REAGENT AND SOLVENT USAGE PER REACTION CYCLE: The quantities of reagents and solvents required per base addition per wafer, and cost of synthesis per base addition were:

0.80 ml acetonitrile
0.08 ml 6.5% dimethylaminopyridine in THF
0.10 ml acetic anhydride/THF/Lutidine
0.26 ml iodine (0.1M in water/lutidine/THF-1:10:4)
0.26 ml 6.3% dichloroacetic acid/dichloreothane
0.03 ml 0.5M tetrazole in acetonitrile
0.03 ml 0.1M 2-cyanoethyl phosphoramidite in acetonitrile Cost per base addition: $0.65. This value is only about ⅓ the cost of synthesis that would pertain to synthesis of these same polynucleotides by the Cruachem PS200 Synthesizer, or by the fully automated Applied Biosystems Model 380A, operated in the standard (prior-art) mode.

TOTAL TIME REQUIRED FOR SYNTHESIS OF 62 POLYNUCLEOTIDES: Synthesis was completed in a single day, over a period of 12 hours. This compares with approximately ten days required to produce this number of polynucleotides using a 3-column, fully automated Applied Biosystems Model 380A Synthesizer, operating at two syntheses per column per day.

Figure 7:
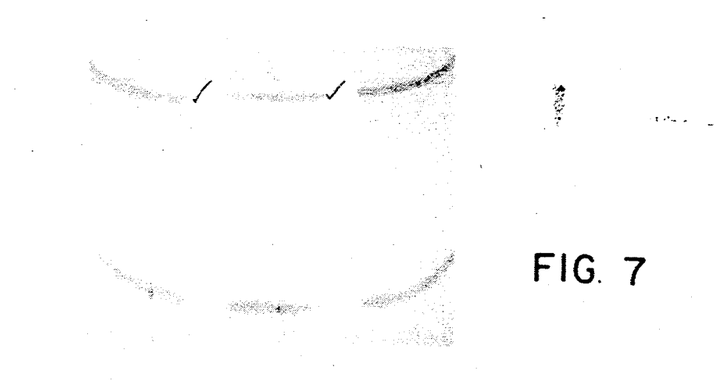
Figure 8:
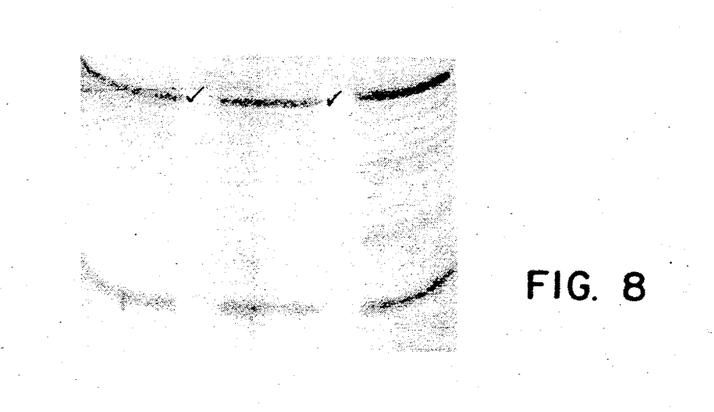

POST-SYNTHESIS DEPROTECTION, DNA PURIFICATION, ANALYSIS: Procedures were the same as those given in Example II. The "UV shadowing" gels illustrated in FIGS. 7 and 8, are representative of those obtained with 20 $A_{260}$ units of crude reaction products formed in this experiment.

Based on the results of UV shadowing gel analyses and quantitation of purified DNA products, the average coupling efficiency during this multiple simultaneous synthesis was estimated to be 92–98%.

COMMENTS: The purified polynucleotides were used in prior-art procedures for oligonucleotide-directed mutagenesis. During this work the DNA products were successfully 5'-phosphorylated (using T4 polynucleotide kinase), annealed to the DNA templates, and elongated by DNA polymerase. Thus, DNA products of high quality were produced, at high yields and at greatly reduced cost and requiring greatly reduced time, compared to prior-art procedures.

Thus, the wafers of the present invention provide for the synthesis of multiple defined-sequenced biopolymers. The geometry of the support material results in high coupling efficiencies, and the rigid wafers facilitate sorting after each reaction cycle. Extremely advantageous are the reduced synthesis cost realized by the present invention and the decreased time required for synthesis of large numbers of biopolymers. The economic and time-saving advantages created by the segmented wafer method should increase demand for the commercial product and fuel future developments in biomedical science.

EXAMPLE IV

Simultaneous Synthesis of Peptides Using the Wafer DNA Synthesis Device

Experimental peptides were synthesized on a Cruachem DNA synthesizer adapted to do segmented peptide synthesis using the new wafers of the present invention. Six wafers were filled with approximately 0.075 g of Kisseniger peptide synthesis resin from Waters Associates. These six wafers were subjected to 9 cycles 1,0 of peptide synthesis; utilizing Fmoc chemistry and fmoc amino acid esters (Int. J. Peptide Protein Res. 13: 35–42 (1979)). At each deblocking and coupling step in the synthesis, the resin was checked for completeness of the reaction using the ninhydrin color test. Samples of resin were taken out of the wafers for amino acid analysis after addition of residues 5 and 10. The ninhydrin color tests were always positive for the deprotection of the peptide and were always negative after coupling of the amino acid. The amino acid analysis of residues 5 and 10 was in agreement with the ninhydrin test and showed that the coupling of the amino acids was successful. This demonstrates the suitability of the wafers for peptide synthesis.

Controlled-pore glass may also be utilized as a substrate for this type of continuous flow segmented peptide synthesis. Because of its good flow characteristics, high loading capacities, and stability, controlled-pore glass allows larger scale synthesis in the segmented wafer than present commercially available resins.

The peptide sequence $NH_4$-G-Y-S-A-L-G-K-S-Y-A-Gresin was synthesized as described above on two different wafers designated 1r10 and 6r10. Amino acid analysis confirmed the synthesis of the expected sequence. The amino acid composition of the peptide synthesized on wafer 1r10 was as follows:

| AA | pmol/ul | Composition | |
|---|---|---|---|
| | | Expected | Observed |
| ser | 1.5 | 2 | 2.02 |
| gly | 1.8 | 3 | 2.43 |
| ala | 1.5 | 2 | 2.02 |
| tyr | 1.3 | 2 | 1.75 |
| leu | 0.96 | 1 | 1.29 |
| lys | 0.85 | 1 | 1.15 |

The amino acid composition of the peptide synthesized on wafer 6r10 was as follows:

| AA | pmol/ul | Composition | |
|---|---|---|---|
| | | Expected | Observed |
| ser | 1.9 | 2 | 2.18 |

-continued

| AA | pmol/ul | Composition | |
|---|---|---|---|
| | | Expected | Observed |
| gly | 2.1 | 3 | 2.41 |
| ala | 1.77 | 2 | 2.03 |
| tyr | 1.8 | 2 | 2.07 |
| leu | 1 | 1 | 1.15 |
| lys | 0.69 | — | 0.79 |

The present invention is well adapted to carry out the objects and attain the ends and the advantages mentioned, as well as those inherent therein. While presently preferred embodiments of the invention have been given for the purpose of disclosure, numerous changes in the details of construction and arrangement of parts can be made which will readily suggest themselves to those skilled in the art and which are encompassed within the spirit of the invention and the scope of the appended claims.

What is claimed is:

1. A modular chemically inert wafer for synthesizing biopolymers, comprising:
    a solid phase support material, derivatized to covalently bind a biopolymer residue;
    a retaining ring having inner and outer walls, for retaining said support material in a chamber formed by the inner walls and coaxially extending there through said retaining ring;
    upper and lower porous means positioned at each end of said retaining ring wherein said porous means allow flow through said retaining ring to said support material and prevent migration of said support material from said retaining ring;
    wherein said solid phase support material, said retaining ring and said porous means are capable of maintaining integrity in the presence of iodine and at pH values above 9.0 and below 3.0; and
    wherein said wafers are adapted to be abuttably stackable in a multiple relationship.

2. The wafer of claim 1, wherein said retaining ring comprises an inner, enclosed reaction chamber for receiving and retaining said support material, said retaining ring being open on both ends.

3. The wafer of claim 2, wherein said porous flow means comprise separate means provided at each end of said retaining ring and extending across said open ends of said retaining ring to enclose said chamber.

4. The wafer of claim 3, wherein said porous flow means are pressure fitted in said retaining ring.

5. The wafer of claim 1, further comprising securing means for securing said porous flow means to said retaining ring.

6. The wafer of claim 5, wherein said securing means is capable of maintaining its integrity in the presence of iodine, at pH values above 9.0 or below 3.0.

7. The wafer of claim 1, wherein said solid phase support material is selected from the group consisting of silica, controlled pore glass, polystyrene-divinyl-benzene, polyamide-Kieselguhr, benzyl-linked polystyrene resins, spacer-linked styrene resins, polyamide resins, and macroreticular resins.

8. The wafer of claim 1, wherein said solid phase support material comprises controlled pore glass.

9. The wafer of claim 1, wherein said solid phase support material comprises a derivatized material with a covalently attached residue.

10. The wafer of claim 1 wherein the porous flow means comprises said solid phase supporting material.

11. The wafer of claim 1, wherein said wafer has a void volume less than the volume of said chamber formed by the inner walls of said retaining ring.

12. The wafer of claim 1, wherein said porous flow means is selected from the group consisting of a fluorocarbon material, fritted glass, scintered glass, titanium and stainless steel.

13. The wafer as claimed in claim 1, wherein the porosity of said flow means is sufficiently large to allow flow through the wafer and sufficiently small to retain said solid phase support material in the wafer.

14. A modular chemically inert wafer for synthesizing biopolymers comprising:
    a solid phase support material, derivatized to covalently bind a biopolymer residue;
    an inner housing ring having inner and outer walls comprising an inner reaction chamber formed by the inner walls of said ring and coaxially extending there through for receiving and retaining said support material, said retaining ring being open at both ends;
    an inert porous membrane positioned at and extending across each of said open ends of said inner retaining ring such that an upper surface of said membrane defines the uppermost surface of said wafer, said membrane having a diameter larger than the outermost diameter of said housing ring so that said membrane extends beyond said outer wall;
    two outer sleeve-like rings having an inner diameter slightly larger than said inner ring and the thickness of said membrane for securing the edges of said membrane between said inner housing ring and said outer sleeve-like rings;
    wherein said solid phase support, inner housing support, inner housing ring, inert porous membrane and outer ring are capable of maintaining integrity in the presence of iodine and at pH values above 9.0 and below 3.0; and
    wherein said wafers are adapted to be abuttably stacked in a multiple relationship.

15. A segmented wafer synthesis device for the synthesis of multiple defined-sequence biopolymers, comprising:
    a solvent/reagent delivery system;
    at least one column connected to said solvent/reagent delivery system to provide solvent and reagent flow through said column; and
    at least one wafer as claimed in claim 1 positioned in said column at which polymeric synthesis occurs.

16. The synthesis device of claim 15, further comprising at least four columns for receiving four reagents, and a plurality of wafers in each column, wherein each of said wafers provides for the synthesis of a defined-sequence biopolymer.

17. A segmented wafer synthesis device for the synthesis of multiple defined-sequence biopolymers, comprising:
    a solvent/reagent delivery system; and
    a plurality of stacked wafers as claimed in claim 1, each of said wafers including a biopolymeric synthesis material and being connected to the next adjacent wafer to form a column, wherein said solvent/reagent delivery system is connected to said column to provide flow through said column.

18. A process for synthesizing biopolymers comprising the steps of:

providing at least one wafer as defined in claim 1;

passing reagents and washing solvents through said at least one wafer to sequentially add at least one biopolymer residue to at least one biopolymer residue bound to said support material;

releasing the completed synthesized biopolymer from said solid support; and collecting the synthesized biopolymer in substantially purified form.

19. The process of claim 18 wherein said reagents and washing solvents are passed through more than one wafer at a time.

20. The process of claim 19 wherein the support material in successive wafers is of varying capacity.

21. The process according to claim 19 wherein said wafers are abuttably stacked in a columnar relationship.

22. The process according to claim 19 wherein said wafers are abuttably stacked to form a column.

23. A process for synthesizing biopolymers, comprising the steps of:

assembling a chemically inert wafer;

using the phosphoramidite method of synthesizing polynucleotides comprising detritylation, condensation, oxidation and capping;

repeating said method to sequentially add nucleotides until the desired biopolymer is completely synthesized; and releasing the completed biopolymer from the solid support, removing protecting groups and recovering said biopolymer in substantially purified form.

24. A process for synthesizing biopolymers comprising the steps of:

making a first stack of more than one modular chemically inert wafer wherein each said wafer is abuttably positioned next to at least one other wafer;

adding at least one biopolymer residue to at least one biopolymer residue bound to support material of said wafer;

removing at least one wafer from said first stack of wafers and placing said removed wafer in a second stack of wafers;

repeating the making of a stack, the adding and removing steps until each desired biopolymer is completely synthesized wherein a different biopolymer residue is added in each stack;

releasing said completed biopolymer from the solid support deprotecting said biopolymers; and recovering said biopolymer in substantially purified form.

25. A modular chemically inert wafer for synthesizing biopolymers, comprising:

a solid phase support material, derivatized to covalently bind a biopolymer residue;

a retaining ring having inner and outer walls, for retaining said support material in a chamber formed by the inner walls and coaxially extending there through said retaining ring;

upper and lower porous means positioned at each end of said retaining ring wherein said porous means allow flow through said retaining ring to said support material and prevent migration of said support material from said retaining ring;

wherein said solid phase support material, said retaining ring, and said upper and lower porous means are capable of maintaining integrity in the presence of iodine, at pH values above 9.0 or below 3.0; and wherein said wafers are adapted to be abuttably stackable in a multiple relationship.

26. A biopolymer synthesizer comprising:

a plurality of reservoirs for synthesis solvents and reagents;

a plurality of reservoirs for biopolymer residue derivatives to be sequentially condensed to form the biopolymer;

a plurality of columns equal to the number of derivative reservoirs, wherein said columns are comprised of at least one chemically inert wafer, said wafer including a solid phase support material derivatized to covalently bind a biopolymer residue, an upper and lower porous means to allow said derivatives and solvent/reagents to flow through said column and a retaining means with inner and outer walls forming a reaction chamber with said porous means;

said derivative reservoirs and solvent/reagent reservoirs being connected to said columns through means for delivering said derivatives and solvent/reagent through controllable valves to supply said derivatives and solvent/reagents to said columns.

27. A biopolymer synthesizer according to claim 26 for polynucleotide synthesis wherein there are four monomer derivative reservoirs and four columns.

28. A biopolymer synthesizer according to claim 26 wherein said column is formed by stacking a plurality of said chemically insert wafers, said stack of wafers forming serially interconnected chambers for holding solid phase support material.

29. A biopolymer synthesizer according to claim 26, further comprising a means for mechanical reassortment of wafers into stacked relationship after each cycle of residue addition.

30. A process for simultaneous chemical synthesis of a multiplicity of biopolymer sequences, comprising the steps of:

assembly of modular chemically inert wafers in abuttably stacked relationship to form a multiplicity of wafer columns;

sequentially passing reagents through wafer columns to effect addition of a different biopolymer residue to growing biopolymers contained within each column;

reassortment of wafers into a new abuttably stacked relationship to provide for synthesis of a multiplicity of biopolymer sequences;

repetition of residue addition steps comprising assembly of columns, biopolymer residue addition, and reassortment of wafers, until synthesis of the desired multiplicity of biopolymer sequences has been achieved.

31. A process for simultaneous chemical synthesis of a multiplicity of biopolymer sequences as described in claim 30; wherein the biopolymer is selected from among the group consisting of polynucleotides, polypeptides, polysaccharides, glycopeptides, lipopolysaccharides, lipopeptides, functional analogs and structural analogs.

32. A column for synthesizing biopolymers comprising:

a plurality of snappers each containing a wafer in the center;

each snapper containing a groove for a sealing ring;

said snappers forming a fluid tight column by compression; and said snappers capable of disengaging and repeatedly forming new columns.

* * * * *